(12) United States Patent
Zheng et al.

(10) Patent No.: US 12,708,268 B2
(45) Date of Patent: Aug. 18, 2026

(54) WEARABLE fNIRS BRAIN IMAGING SYSTEM

(71) Applicant: BEIHANG UNIVERSITY, Beijing (CN)

(72) Inventors: Dezhi Zheng, Beijing (CN); Feiyang Zhang, Beijing (CN); Chun Hu, Beijing (CN); Shuailei Zhang, Beijing (CN); Rui Na, Beijing (CN); Shangchun Fan, Beijing (CN)

(73) Assignee: BEIHANG UNIVERSITY, Beijing (CN)

(*) Notice: Subject to any disclaimer, the term of this patent is extended or adjusted under 35 U.S.C. 154(b) by 714 days.

(21) Appl. No.: 18/033,553

(22) PCT Filed: Jul. 14, 2021

(86) PCT No.: PCT/CN2021/106182
§ 371 (c)(1),
(2) Date: Apr. 24, 2023

(87) PCT Pub. No.: WO2022/088760
PCT Pub. Date: May 5, 2022

(65) Prior Publication Data

US 2023/0389798 A1 Dec. 7, 2023

(30) Foreign Application Priority Data

Oct. 27, 2020 (CN) ......................... 202011161898.2

(51) Int. Cl.
*A61B 5/00* (2006.01)
*A61B 5/1455* (2006.01)

(52) U.S. Cl.
CPC .......... *A61B 5/0042* (2013.01); *A61B 5/0035* (2013.01); *A61B 5/0075* (2013.01); *A61B 5/14553* (2013.01); *A61B 5/6814* (2013.01)

(58) Field of Classification Search
CPC ... A61B 5/0042; A61B 5/0035; A61B 5/0075; A61B 5/14553; A61B 5/6814; A61B 5/291; A61B 5/4064; A61B 5/6803
See application file for complete search history.

(56) References Cited

U.S. PATENT DOCUMENTS

| | | | | |
|---|---|---|---|---|
| 9,946,344 | B2 * | 4/2018 | Ayaz | A61B 5/14553 |
| 11,941,857 | B2 * | 3/2024 | Dehghani | G06V 10/14 |

(Continued)

FOREIGN PATENT DOCUMENTS

| | | |
|---|---|---|
| CN | 103156620 | 6/2013 |
| CN | 103610467 | 3/2014 |

(Continued)

*Primary Examiner* — Sanjay Cattungal

(57) ABSTRACT

A wearable fNIRS brain imaging system, including a light source-photoelectric detector module, a control and wireless transmission module, a power source module, and an upper computer; the system is able to solve the problems in a wearable fNIRS brain imaging system or an EEG-fNIRS multi-modal brain imaging system where the relative position of a probe cannot be freely adjusted and a detection region is limited; in the present system, the relative positions of a light source probe and a photoelectric detector can be freely adjusted according to actual circumstances, and the distance between the two is automatically measured; a brain electricity sensor may be installed at the periphery of the light source probe and a bottom face of a cylindrical casing of the photoelectric detector, and distance therebetween synchronously changes with the probe, implementing EEG-fNIRS multi-modal brain imaging, and also able to capture brain electrical signals of differing densities.

10 Claims, 5 Drawing Sheets

(56) References Cited

U.S. PATENT DOCUMENTS

| | | | | |
|---|---|---|---|---|
| 11,950,879 | B2 * | 4/2024 | Field | A61B 5/4064 |
| 11,969,259 | B2 * | 4/2024 | Seidman | G01J 1/0425 |
| 2005/0228291 | A1 | 10/2005 | Chance | |
| 2008/0247618 | A1 * | 10/2008 | Laine | G06T 7/0012<br>382/128 |
| 2013/0102907 | A1 * | 4/2013 | Funane | A61B 5/0042<br>600/476 |
| 2014/0276069 | A1 * | 9/2014 | Amble | A61B 8/4488<br>600/447 |
| 2017/0172447 | A1 | 6/2017 | Mitra et al. | |
| 2017/0281014 | A1 * | 10/2017 | von Luehmann | A61B 5/14551 |
| 2018/0153472 | A1 * | 6/2018 | Funane | A61B 5/6814 |
| 2018/0220968 | A1 | 8/2018 | Funane et al. | |
| 2019/0201691 | A1 * | 7/2019 | Poltorak | A61B 5/374 |
| 2025/0134405 | A1 * | 5/2025 | Akbari | A61B 5/6841 |

FOREIGN PATENT DOCUMENTS

| | | | |
|---|---|---|---|
| CN | 104207770 | A | 12/2014 |
| CN | 106725464 | | 5/2017 |
| CN | 108186028 | | 6/2018 |
| CN | 108186028 | A | 6/2018 |
| CN | 109528215 | A | 3/2019 |

* cited by examiner

WEARABLE fNIRS BRAIN IMAGING SYSTEM

TECHNICAL FIELD

This invention generally relates to the technical field of biomedical engineering and brain imaging, and more particularly, to a wearable fNIRS brain imaging system capable of adjusting the probe position while measuring the distance.

BACKGROUND

Near-infrared light is capable of reaching biological tissues at a certain depth. The near-infrared light of 600-900 nm is mainly absorbed by the oxygenated hemoglobin (HbO2) and reduced hemoglobin (Hb) in the blood. the functional near infrared spectroscopy (fNIRS) technology adopts the near-infrared light to irradiate the brain, wherein a photoelectric detector is placed at several centimeters from the light source to receive the emitted light. The emitted light carries the concentration information of HbO2 and Hb in the cerebral cortex. Neurological activities in the brain may cause a relative increase in local HbO2 concentration and a relative decrease in Hb concentration within a short period of time. Therefore, through measuring the concentration variation of HbO2 and Hb in the cerebral cortex, the functional activities of the brain are reflected and the brain functional imaging is realized. The fNIRS brain imaging system achieves a real-time imaging, high safety, low cost and high temporal/spatial resolution, which has been extensively used in neuroscience and clinical medicine.

When using the fNIRS brain imaging system, a collection cap is normally worn on a user's head, and then the light source probe and photoelectric detector are inserted into the fixed holes pre-formed in the collection cap. The light source emits near-infrared light to the brain through the head skin, which is scattered by tissues, received by a photoelectric detector and then converted into electrical signals. The electrical signals are transmitted to a back-end processing system and converted into a brain blood oxygen concentration signal. Traditional back-end processing systems are clumsy and heavy, requiring fixed placement such that the user's range of activity is severely restricted. Presently, through reducing the volume of back-end processing systems, the portability and wearability of fNIRS brain imaging systems are significantly improved. For instance, the NIRSPORT 2 developed by NIRx company allows a user to tie the back-end processing system to his waist, and the WOT-100 developed by Hitachi Corporation allows the entire system to be directly worn on the user's head.

However, in traditional wearable fNIRS brain imaging systems, the positions of holes formed in the collection cap hole or probe are fixed, failing to enable users to freely adjust the relative position of the light source probe and the photoelectric detector according to the actual circumstances. Moreover, the cerebral region able to be detected is located between the light source probe and the photoelectric detector, resulting in limited detection region of the system.

In recent years, some fNIRS brain imaging systems allowing the probe position to be adjusted are sold on the market, such as fNIRS brain imaging systems allowing the distance between the photoelectric detector and the head skin to be adjusted, as well as fNIRS brain imaging systems that use flexible hollow head covers. However, due to the connection components fixedly arranged between the light source probe and the photoelectric detector in these systems, the adjustment ability is poor, resulting in the failure of enlarging the detection region and adjusting the angle and distance between the light source probe and the photoelectric detector in a wider range.

SUMMARY

The purpose of the present invention is to provide a wearable fNIRS brain imaging system capable of adjusting the probe position while measuring the distance. The system of the present invention is able to solve the problems in a wearable fNIRS brain imaging system or an EEG-fNIRS multi-modal brain imaging system where the relative position of a probe cannot be freely adjusted and a detection region is limited.

To achieve the above purpose, the present invention adopts the following technical solution:

A wearable fNIRS brain imaging system, comprising a light source-photoelectric detector module, a control and wireless transmission module, a power source module, and an upper computer, wherein the light source-photoelectric detector module comprises at least one light source-photoelectric detector assembly, and each light source-photoelectric detector assembly comprises a light source probe and a photoelectric detector embedded in the cylindrical casing, wherein the light source probe and the cylindrical casing of the photoelectric detector are connected through a telescopic pull rod, and the telescopic pull rod is capable of horizontally and vertically rotating around the photoelectric detector, wherein the light source probe is capable of rotating in three directions around the telescopic pull rod, and the telescopic pull rod is provided with at least one limiting hole for adjusting the distance between the light source probe and the photoelectric detector, wherein the control and wireless transmission module adopts an ARM, DSP or FPGA as the main control chip, which drives the light source-photoelectric detector module to operate and wirelessly transmits signals to the upper computer by means of a built-in WIFI or Bluetooth module, wherein the power supply module supplies power to the light source-photoelectric detector module and the control and wireless transmission module, wherein the upper computer receives the signal output by the control and wireless transmission module and performs signal processing and analysis.

In another preferred embodiment of the present invention, one end of the telescopic pull rod is connected to the casing of the photoelectric detector by means of the dual-shaft hinge, and the angle formed between the light source probe and the photoelectric detector is adjusted by means of the dual-shaft hinge. The other end of the telescopic pull rod is connected to the casing of the light source probe by means of the spherical hinge, and the light source probe emits light perpendicular to a user's head through the spherical hinge.

In another preferred embodiment of the present invention, the telescopic pull rod is internally provided with a linear potentiometer. According to the output voltage of a detection circuit in the control and wireless transmission module, measuring the distance between the light source probe and the photoelectric detector, comprising:

Step 1: setting the stage length of the telescopic pull rod from small to large as $L_1, L_2, \ldots L_i, \ldots L_n$, the resistance value of the corresponding linear potentiometer as $R_1, R_2, \ldots R_i, \ldots R_n$, and the theoretical output voltage of the corresponding detection circuit as $U_1, U_2, \ldots U_i, \ldots U_n$, wherein i represents the stage number, n represents the number of stages, and $n \geq 2$; setting the voltage to be detected as U, and if $0.9U_1 \leq U \leq 1.1U_n$, making a=n and b=1, wherein a represents the highest stage to be detected and b represents the lowest stage to be detected, and entering step 2; if L=−1, namely, a failure of the detection circuit occurs, discontinuing the measurement;

Step 2: make i=[(a+b)/2], wherein [L] represents rounding; if i=1, entering step 3, if i=n, entering step 4, and if 1<i<n, entering step 5;

Step 3: if $U>(U_1+U_2)/2$, making b=i+1 and repeating step 2; if $0.9U_1 \leq U \leq (U_1+U_2)/2$ and $L=L_1$, discontinuing the measurement;

Step 4: if $U<(U_{n-1}+U_n)/2$, making a=i−1 and repeating step 2; if $(U_{n-1}+U_n)/2 \leq U \leq 1.1U_n$ and $L=L_n$, discontinuing the measurement;

Step 5: if $U<(U_{i-1}+U_i)/2$, making a=i−1 and repeating step 2; if $U>(U_i+U_{i+1})/2$, making b=i+1 and repeating step 2; if $(U_{i-1}+U_i)/2 \leq U \leq (U_i+U_{i+1})/2$ and $L=L_i$, discontinuing the measurement.

In another preferred embodiment of the present invention, five limiting holes are formed in the telescopic pull rod, and the length of the telescopic pull rod may be adjusted in five stages including 20 mm, 25 mm, 30 mm, 35 mm and 40 mm. The telescopic pull rod is used for adjusting the distance between the light source probe and the photoelectric detector.

In another preferred embodiment of the present invention, holes are formed in the bottom surface of the cylindrical casing of the light source probe and the photoelectric detector to mount electroencephalogram sensors for realizing the EEG-fNIRS multi-modal brain imaging.

In another preferred embodiment of the present invention, eight holes are formed in the bottom surface of the cylindrical casing of each light source probe and photoelectric detector for mounting dry electrode electroencephalogram sensors, thereby collecting electroencephalogram signals. The dry electrode electroencephalogram sensors adopt a probe structure with an adjustable length.

In another preferred embodiment of the present invention, the light source-photoelectric detector assembly comprises a light emitting diode, a telescopic pull rod and an avalanche photodiode.

In another preferred embodiment of the present invention, the light source-photoelectric detector assembly comprises four light source probes, four telescopic pull rods and a photoelectric detector; alternatively, the light source-photoelectric detector assembly comprises two light source probes, two telescopic pull rods and a photoelectric detector.

In another preferred embodiment of the present invention, the fixed length of the linear potentiometer is 20 mm, and the resistance value $R_0$=2 kΩ. The moving length of the linear potentiometer is 20 mm, and the maximum resistance value $R_1$=2 kΩ. When the pull rod stretches and contracts, the resistance variation of the linear potentiometer ranges from 2-4 kΩ.

In another preferred embodiment of the present invention, the power supply module adopts a lithium battery to supply power.

Compared with the prior art, the present invention has the following advantages:

1. In traditional fNIRS brain imaging systems, the distance between the light source probe and the photoelectric detector is fixed; when taking into account both the penetrability depth and the signal-to-noise ratio, the distance between the two is normally 30 mm; however, different persons have different brain shapes, and even for a same person, the thickness of each layer of tissue in different locations of the brain is also different; therefore, the optimal distance also varies from person to person and from "place" to "place" (different brain locations); in addition, distance is also an important parameter for calculating the cerebral blood oxygen concentration; when the distance is variable, it is necessary to measure the distance for facilitating a subsequent calculation of cerebral blood oxygen concentration; through adopting the present invention, the relative positions of a light source probe and a photoelectric detector can be freely adjusted according to actual circumstances, and the distance between the two is automatically measured, which can reduce measurement error of a brain blood-oxygen signal, and allows for flexible adjustment of a cerebral detection region;
2. The system of the present invention can harmonize with brain electrical signal detection, a brain electricity sensor may be installed at the periphery of the light source probe and a bottom face of a cylindrical casing of the photoelectric detector, and distance therebetween synchronously changes with the probe, implementing EEG-fNIRS multi-modal brain imaging, and also able to capture cerebral electrical signals of differing densities.

BRIEF DESCRIPTION OF THE DRAWINGS

To clearly illustrate the embodiments of the present invention or the technical solutions in the prior art, drawings that need to be used in the embodiments are briefly described below, which allow the features and benefits of the present invention to be clearly understood. These drawings are used for an illustrative purpose instead of limiting the present invention. For those skilled in the art, other drawings may be obtained based on these drawings without paying creative labor.

DETAILED DESCRIPTION

To clearly understand the above purposes, features and benefits of the present invention, drawings and embodiments are combined hereinafter to further elaborate the technical solution of the present invention. It should be noted that the embodiments of the present invention and the features in the embodiments may be combined with each other without conflict.

Specific details are set forth in the following description to facilitate a full understanding of the present invention. However, the present invention may also be implemented in other ways different from those described herein. Therefore, the scope of the present invention is not limited by the embodiments described below.

Figure 1:
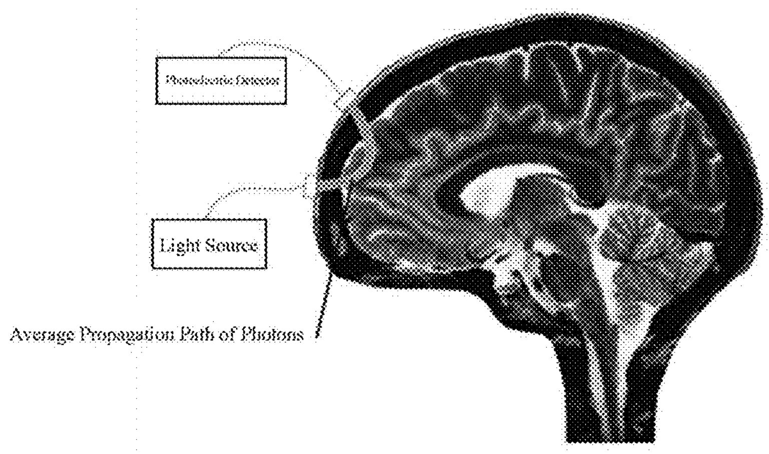
FIG. 1 is a principle diagram illustrating the fNIRS system.

As shown in FIG. 1, the functional near infrared spectroscopy (fNIRS) technology adopts the near-infrared light to irradiate the brain, wherein a photoelectric detector is placed at several centimeters from the light source to receive the emitted light.

In traditional fNIRS brain imaging systems, the distance between the light source probe and the photoelectric detector is fixed. When taking into account both the penetrability depth and the signal-to-noise ratio, the distance between the two is normally 30 mm. However, different persons have different brain shapes, and even for a same person, the thickness of each layer of tissue in different locations of the brain is also different. Therefore, the optimal distance also varies from person to person and from "place" to "place" (different brain locations). In addition, distance is also an important parameter for calculating the cerebral blood oxygen concentration. When the distance is variable, it is necessary to measure the distance for facilitating a subsequent calculation of cerebral blood oxygen concentration. Through adopting the present invention, the relative positions of a light source probe and a photoelectric detector can be freely adjusted according to actual circumstances, and the distance between the two is automatically measured, which can reduce measurement error of a brain blood-oxygen signal, and allows for flexible adjustment of a cerebral detection region.

Additionally, the system of the present invention can harmonize with brain electrical signal detection, a brain electricity sensor may be installed at the periphery of the light source probe and a bottom face of a cylindrical casing of the photoelectric detector, and distance therebetween synchronously changes with the probe, implementing EEG-fNIRS multi-modal brain imaging, and also able to capture cerebral electrical signals of differing densities.

Figure 2:
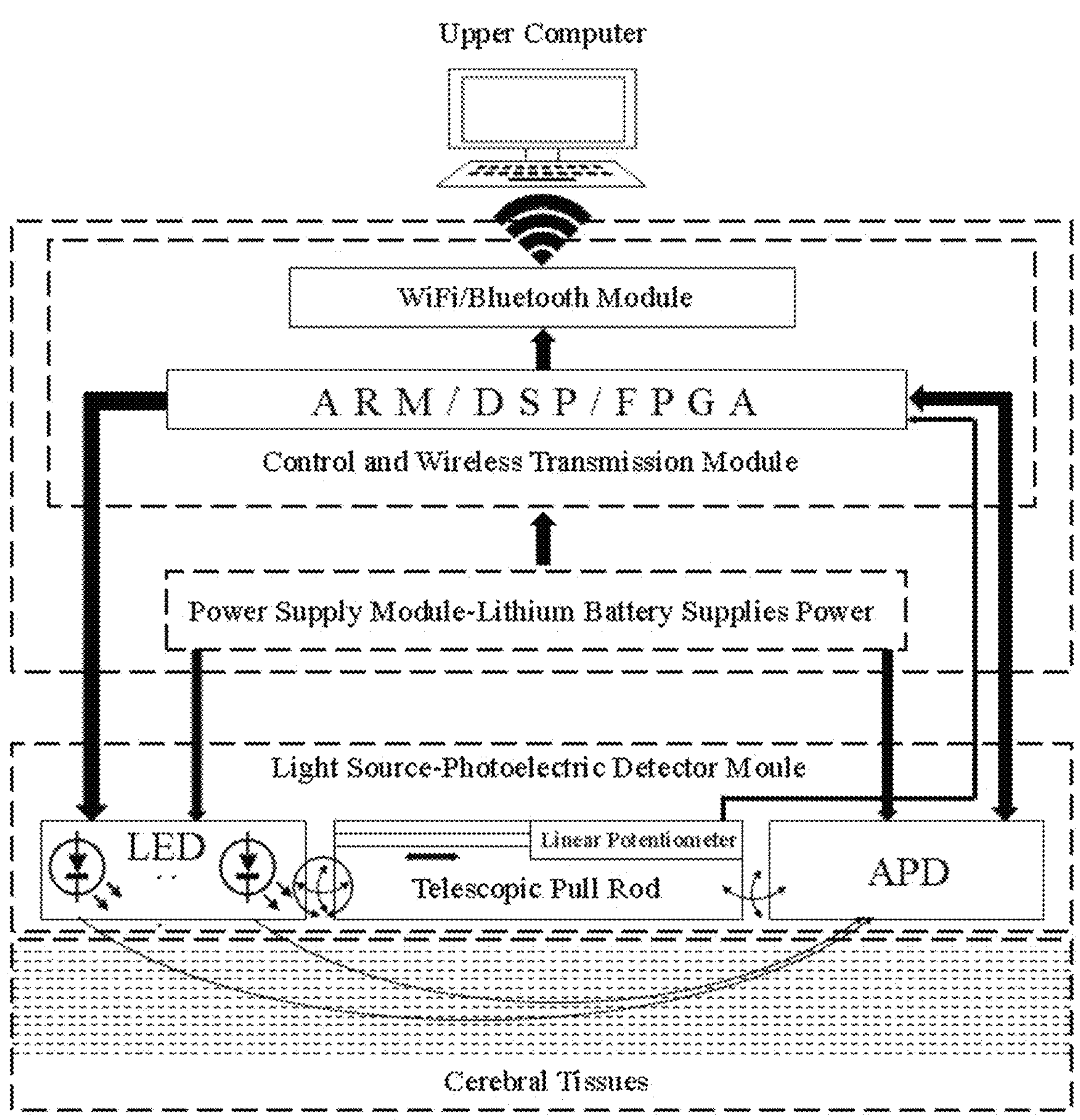
FIG. 2 is a schematic diagram illustrating an exemplary structure of the wearable fNIRS brain imaging system of the present invention.

Specifically, as shown in FIG. 2, a wearable fNIRS brain imaging system, comprising a light source-photoelectric detector module, a control and wireless transmission module, a power source module, and an upper computer. The light source-photoelectric detector module comprises at least one light source-photoelectric detector assembly, and each light source-photoelectric detector assembly comprises a light source probe and a photoelectric detector embedded in the cylindrical casing. The light source probe and the cylindrical casing of the photoelectric detector are connected through a telescopic pull rod, and the telescopic pull rod is capable of horizontally and vertically rotating around the photoelectric detector. The light source probe is capable of rotating in three directions around the telescopic pull rod, and the telescopic pull rod is provided with at least one limiting hole for adjusting the distance between the light source probe and the photoelectric detector. Through adopting the telescopic pull rod, a multi-stage distance adjustment is realized.

The control and wireless transmission module adopts an ARM, DSP or FPGA as the main control chip, which drives the light source-photoelectric detector module to operate while and wirelessly transmitting the brightness control signal of the light source probe, the electric signal received by the photoelectric detector, the measurement signal output by a linear potentiometer and the electroencephalogram signal detected by an electroencephalogram sensor to the upper computer by means of a built-in WIFI or Bluetooth module.

The power supply module supplies power to the light source-photoelectric detector module and the control and wireless transmission module.

The upper computer receives the signal output by the control and wireless transmission module, converts the light intensity variation and the distance between the light source probe and the photoelectric detector into a brain blood oxygen signal, and performs signal processing and analysis using the brain blood oxygen signal and the electroencephalogram signal.

In the present invention, a dual-shaft hinge and a spherical hinge are used for connection to achieve the angle adjustment. One end of the telescopic pull rod is connected to the casing of the photoelectric detector by means of the dual-shaft hinge. The telescopic pull rod is capable of rotating in two directions around the photoelectric detector, and the angle formed between the light source probe and the photoelectric detector is adjusted by means of the dual-shaft hinge. The other end of the telescopic pull rod (the moving end of the linear potentiometer) is connected to the casing of the light source probe by means of the spherical hinge. The light source probe is capable of rotating in three directions around the telescopic pull rod, and the light source probe emits light perpendicular to a user's head through the spherical hinge. Holes are formed between the spherical hinge and the casing of the light source probe, and screws are inserted into the holes. After the angle of the light source probe is adjusted, the screws are screwed to fix the spherical hinge. Holes are formed in a collection cap according to the position of the adjusted light source probe, and then the collection cap is worn on the user's head to fix the light source probe. The angle formed between the light source probe and the photoelectric detector can be freely adjusted through the dual-shaft hinge and the spherical hinge, and the relative position of the light source probe and the user's head can also be adjusted, enabling the light source probe to directly emit near-infrared light to the user's head such that the measurement error is significantly reduced.

Because distance is an important parameter for calculating the cerebral blood oxygen concentration, when the distance is variable, it is necessary to measure the distance for facilitating a subsequent calculation of cerebral blood oxygen concentration. The telescopic pull rod is internally provided with a linear potentiometer. The resistance value linearly varies along with the variation of the distance between the light source probe and the photoelectric detector, and the output voltage is produced by a detection circuit in the control and wireless transmission module, so that automatic measurement of the distance between the light source probe and the photoelectric detector is realized. Specifically, measuring the distance between the light source probe and the photoelectric detector, comprising:

Step 1: setting the stage length of the telescopic pull rod from small to large as $L_1, L_2, \ldots L_i, \ldots L_n$, the resistance value of the corresponding linear potentiometer as $R_1, R_2, \ldots R_i, \ldots R_n$, and the theoretical output voltage of the corresponding detection circuit as $U_1, U_2, \ldots U_i, \ldots U_n$, wherein i represents the stage number, n represents the number of stages, and $n \geq 2$; setting the voltage to be detected as U, and if $0.9U_1 \leq U \leq 1.1U_n$, making a=n and b=1, wherein a represents the highest stage to be detected and b represents the lowest stage to be detected, and entering step 2; if $L=-1$, namely, a failure of the detection circuit occurs, discontinuing the measurement;

Step 2: make i=[(a+b)/2], wherein [•] represents rounding; if i=1, entering step 3, if i=n, entering step 4, and if 1<i<n, entering step 5;

Step 3: if $U>(U_1+U_2)/2$, making b=i+1 and repeating step 2; if $0.9U_1 \le U \le (U_1+U_2)/2$ and $L=L_1$, discontinuing the measurement;

Step 4: if $U<(U_{n-1}+U_n)/2$, making a=i−1 and repeating step 2; if $(U_{n-1}+U_n)/2 \le U \le 1.1U_n$ and $L=L_n$, discontinuing the measurement;

Step 5: if $U<(U_{i-1}+U_i)/2$, making a=i−1 and repeating step 2; if $U>(U_i+U_{i+1})/2$, making b=i+1 and repeating step 2; if $(U_{i-1}+U_i)/2 \le U \le (U_i+U_{i+1})/2$ and $L=L_i$, discontinuing the measurement.

Five limiting holes are formed in the telescopic pull rod, and the length of the telescopic pull rod may be adjusted in five stages including 20 mm, 25 mm, 30 mm, 35 mm and 40 mm. The telescopic pull rod is used for adjusting the distance between the light source probe and the photoelectric detector.

Holes are formed in the bottom surface of the cylindrical casing of the light source probe and the photoelectric detector to mount electroencephalogram (EEG) sensors for realizing the EEG-fNIRS multi-modal brain imaging. The distance between the electroencephalogram sensors can also synchronously vary along with the variation of distance between the probes, thereby achieving the collection of electroencephalogram signals with different densities while making the system more flexible.

Eight holes are formed in the bottom surface of the cylindrical casing of each light source probe and photoelectric detector for mounting dry electrode electroencephalogram sensors, thereby collecting electroencephalogram signals while the measuring the cerebral blood oxygen concentration. The dry electrode electroencephalogram sensors adopt a probe structure with an adjustable length such that the sensors are in good contact with the head skin.

In some embodiments, the light source-photoelectric detector assembly comprises a light emitting diode, a telescopic pull rod and an avalanche photodiode.

In some embodiments, the light source-photoelectric detector assembly comprises four light source probes, four telescopic pull rods and a photoelectric detector; alternatively, the light source-photoelectric detector assembly comprises two light source probes, two telescopic pull rods and a photoelectric detector.

Figure 3:
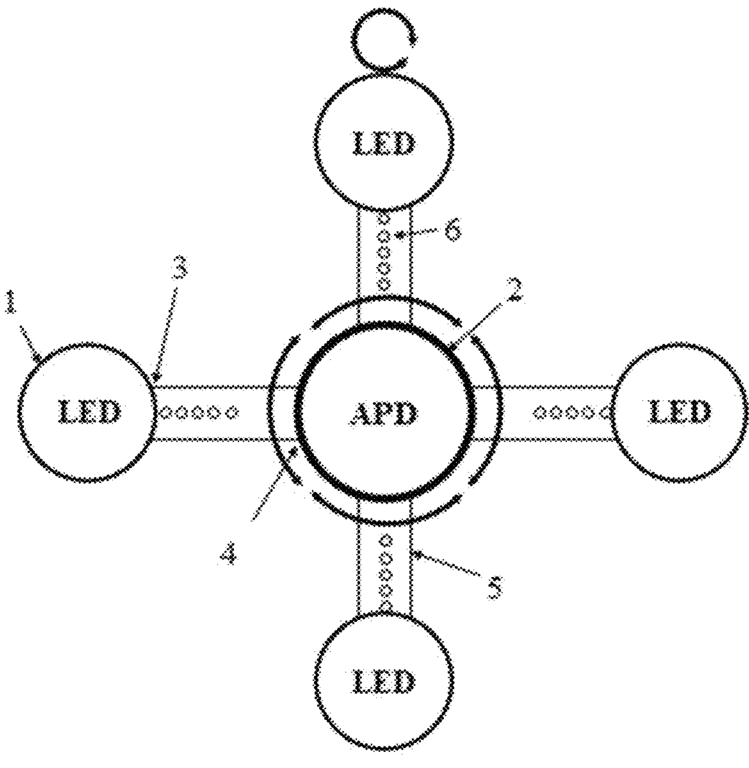
FIG. 3 is a schematic diagram illustrating an exemplary structure of the light source-photoelectric detector assembly of the present invention.
Figure 4:
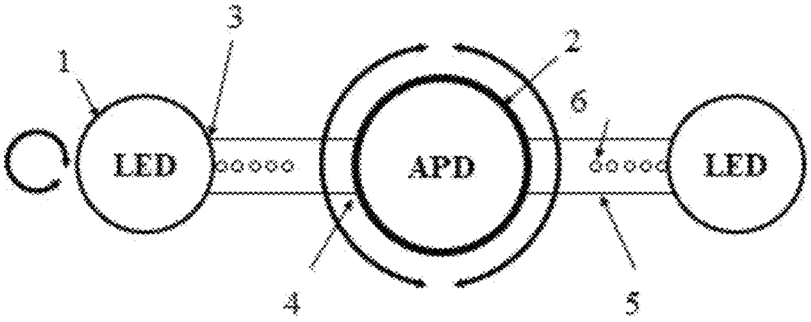
FIG. 4 is a schematic diagram illustrating another exemplary structure of the light source-photoelectric detector assembly of the present invention.

Preferably, as shown in FIGS. 3 and 4, the light source-photoelectric detector assembly comprises four light emitting diodes (LEDs), four telescopic pull rods and an avalanche photodiode (APD), which is named 4S1D; alternatively, the light source-photoelectric detector assembly comprises two light emitting diodes (LEDs), two telescopic pull rods and an avalanche photodiode (APD), which is named 2S1D. More specifically, the LED and the APD are respectively embedded in the cylindrical casings, the two casings of the LED and the APD are connected by a telescopic pull rod, and a linear potentiometer is arranged in the telescopic pull rod for automatically measuring the distance between the LED and the APD. The casing of the LED is connected to the telescopic pull rod through a spherical hinge, and the casing of the APD is connected to the telescopic pull rod through a double-shaft hinge. The angle formed between the LED and the APD is adjusted through the double-shaft hinge, and the distance between the LED and the APD is adjusted through the telescopic pull rod. The spherical hinge enables the LEDs to emit light perpendicular to the head skin. The LEDs emit near-infrared light with two wavelengths of 760 nm and 850 nm to implement the measurement.

Figure 5:
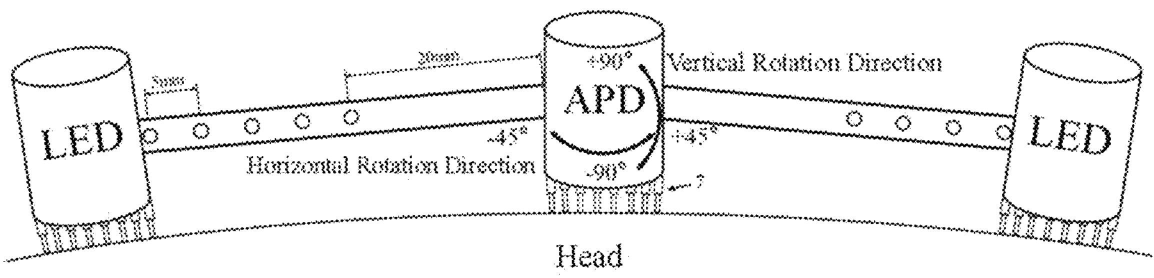
FIG. 5 is a schematic diagram illustrating the rotating angle of the telescopic pull rod of the structure shown in FIG. 3.

As shown in FIG. 5, for a 4S1D structure, the horizontal rotation angle of the telescopic pull rod around the APD ranges from −45° to 45°, and the vertical rotation angle of the telescopic pull rod around the APD ranges from −90° to 90°.

Figure 6:
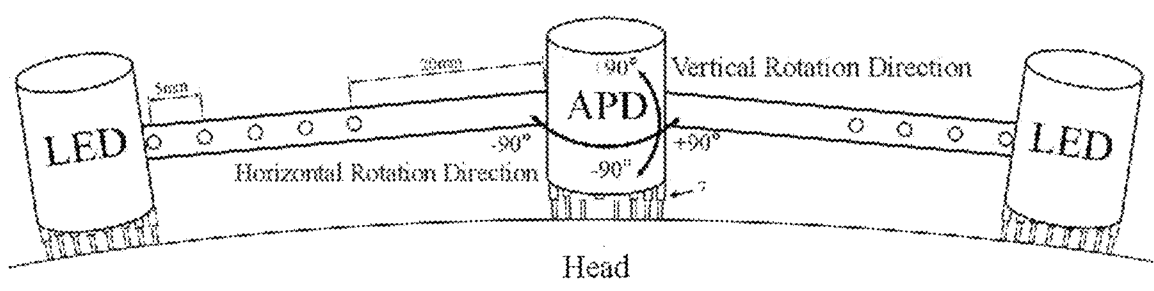
FIG. 6 is a schematic diagram illustrating the rotating angle of the telescopic pull rod of the structure shown in FIG. 4.

As shown in FIG. 6, for a 2S1D structure, the horizontal rotation angle of the telescopic pull rod around the APD ranges from −90° to 90°, and the vertical rotation angle of the telescopic pull rod around the APD ranges from −90° to 90°.

Figure 7:
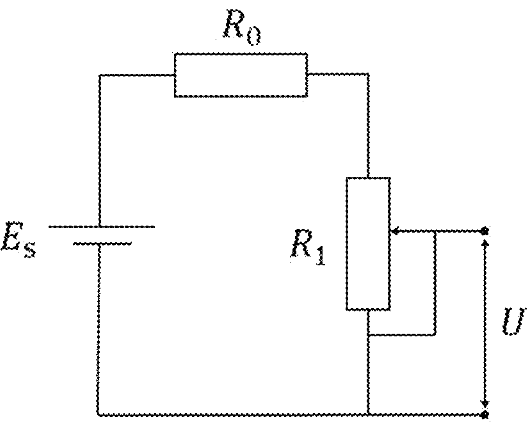
FIG. 7 is a schematic diagram illustrating the detection circuit of the linear potentiometer.

As shown in FIG. 7, the fixed length of the linear potentiometer is 20 mm, and the resistance value R0=2 kΩ. The moving length of the linear potentiometer is 20 mm, and the maximum resistance value R1=2 kΩ. When the pull rod stretches and contracts, the resistance variation of the linear potentiometer ranges from 2-4 kΩ.

The power supply module adopts a lithium battery to supply power such that a cable is avoided, significantly reducing the size and weight of the system.

In the description of the present invention, unless it is clearly stated, the terms "installation", "connection" and "fixed" shall be understood in a broad sense. For instance, it may be a fixed connection, a detachable connection, a mechanical connection, an electrical connection, a direct connection, an indirect connection through an intermediate medium, an internal connection of two components or an interaction between two components. For those skilled in the art, the specific meanings of the above terms in the present invention may be understood according to specific circumstances.

In the description of the present invention, unless it is clearly stated, the first feature being "above" or "below" the second feature may indicate that the first feature and the second feature are in direct contact or in indirect contact through other features between them. Moreover, the first feature being "above" the second feature may indicate that the first feature is directly above and obliquely above the second feature, or may simply indicate that the horizontal height of the first feature is higher than that of the second feature. The first feature being "below" the second feature may indicate that the first feature is directly below and obliquely below the second feature, or may simply indicate that the horizontal height of the first feature is lower than that of the second feature.

In addition, the terms "first", "second", "third" and "fourth" are used for descriptive purposes only and cannot be understood as the indication or implication of relative importance. In the description of the present invention, unless it is clearly stated, "a plurality of" means two or more.

The above is merely a preferred embodiment of the present invention and is not intended to limit the present invention. For those skilled in the art, various modifications and improvements may be made according to the specification of the present invention. Therefore, any modification, equivalent replacement, improvement made within the spirit and principles of the present invention shall fall into the scope of the present invention.

What is claimed is:

1. A wearable fNIRS brain imaging system, comprising:

a light source-photoelectric detector module comprising at least one light source-photoelectric detector assembly, wherein the at least one light source-photoelectric detector assembly comprises a light source probe and a photoelectric detector, each embedded in a cylindrical casing, a control and wireless transmission module comprising a main control chip selected from ARM, DSP, or FPGA, and a built-in WIFI or Bluetooth module, a power source, and an upper computer, wherein the cylindrical casing of the light source probe and the cylindrical casing of the photoelectric detector are connected through a telescopic pull rod, wherein the telescopic pull rod is capable of horizontally and vertically rotating around the photoelectric detector, wherein the light source probe is capable of rotating in three directions around the telescopic pull rod, wherein the telescopic pull rod is provided with at least one limiting hole for adjusting a distance between the light source probe and the photoelectric detector, wherein the main control chip drives the light source-photoelectric detector module to operate and wirelessly transmits signals to the upper computer by means of the built-in WIFI or Bluetooth module, wherein the power source supplies power to the light source-photoelectric detector module and the control and wireless transmission module, wherein the upper computer receives the signals output by the control and wireless transmission module and performs signal processing and analysis, wherein one end of the telescopic pull rod is connected to the cylindrical casing of the photoelectric detector by means of a dual-shaft hinge, wherein an angle formed between the light source probe and the photoelectric detector is adjusted by means of the dual-shaft hinge, wherein another end of the telescopic pull rod is connected to the cylindrical casing of the light source probe by means of a spherical hinge, and the light source probe emits light perpendicular to a user's head through the spherical hinge.

2. The wearable fNIRS brain imaging system of claim 1, wherein the telescopic pull rod is internally provided with a linear potentiometer, wherein according to an output voltage of a detection circuit in the control and wireless transmission module, measuring the distance between the light source probe and the photoelectric detector, comprising:

step 1: setting a set of stage lengths of the telescopic pull rod from small to large as $L_1, L_2, \ldots L_i, \ldots L_n$, a set of resistance values of the linear potentiometer corresponding to each stage length as $R_1, R_2, \ldots R_i, \ldots R_n$, and a set of theoretical output voltages of the detection circuit corresponding to each resistance value as $U_1, U_2, \ldots U_i, \ldots U_n$, wherein i represents a stage number, n represents the number of stages, and $n \geq 2$; setting a voltage to be detected as U, and if $0.9U_1 \leq U \leq 1.1U_n$, making a=n and b=1, wherein a represents the highest stage to be detected and b represents the lowest stage to be detected, and entering step 2; if L=−1, namely, a failure of the detection circuit occurs, discontinuing the measurement;

step 2: make $i=[(a+b)/2]$, wherein $[\cdot]$ represents rounding; if i=1, entering step 3, if i=n, entering step 4, and if 1<i<n, entering step 5;

step 3: if $U>(U_1+U_2)/2$, making b=i+1 and repeating step 2; if $0.9U_1 \leq U \leq (U_1+U_2)/2$ and $L=L_1$, discontinuing the measurement;

step 4: if $U<(U_{n-1}+U_n)/2$, making a=i−1 and repeating step 2; if $(U_{n-1}+U_n)/2 \leq U \leq 1.1U_n$ and $L=L_n$, discontinuing the measurement;

step 5: if $U<(U_{i-1}+U_i)/2$, making a=i−1 and repeating step 2; if $U>(U_i+U_{i+1})/2$, making b=i+1 and repeating step 2; if $(U_{i-1}+U_i)/2 \leq U \leq (U_i+U_{i+1})/2$ and $L=L_i$, discontinuing the measurement.

3. The wearable fNIRS brain imaging system of claim 1, wherein five limiting holes are formed in the telescopic pull rod, wherein the length of the telescopic pull rod may be adjusted in five stages at 20 mm, 25 mm, 30 mm, 35 mm and 40 mm, wherein the telescopic pull rod is used for adjusting the distance between the light source probe and the photoelectric detector.

4. The wearable fNIRS brain imaging system of claim 1, wherein a bottom surface of the cylindrical casing of the light source probe, and a bottom surface of the cylindrical casing of the photoelectric detector are each provided with holes to mount electroencephalogram sensors for realizing the EEG-fNIRS multi-modal brain imaging.

5. The wearable fNIRS brain imaging system of claim 1, wherein a bottom surface of the cylindrical casing of the light source probe, and a bottom surface of the cylindrical casing of the photoelectric detector are each provided with eight holes to mount dry electrode electroencephalogram sensors for collecting electroencephalogram signals, wherein each of the dry electrode electroencephalogram sensors adopts a probe structure with an adjustable length.

6. The wearable fNIRS brain imaging system of claim 1, wherein the at least one light source-photoelectric detector assembly further comprises a light emitting diode, a telescopic pull rod and an avalanche photodiode.

7. The wearable fNIRS brain imaging system of claim 1, wherein the at least one light source-photoelectric detector assembly further comprises four light source probes, four telescopic pull rods and a photoelectric detector, wherein alternatively, the at least one light source-photoelectric detector assembly further comprises two light source probes, two telescopic pull rods and a photoelectric detector.

8. The wearable fNIRS brain imaging system of claim 2, wherein the fixed length of the linear potentiometer is 20 mm, and the resistance value $R_0$=2 kΩ, wherein the moving length of the linear potentiometer is 20 mm, and the maximum resistance value $R_1$=2 kΩ, wherein when the pull rod stretches and contracts, the resistance variation of the linear potentiometer ranges from 2-4 kΩ.

9. The wearable fNIRS brain imaging system of claim 1, wherein the power source adopts a lithium battery to supply power.

10. The wearable fNIRS brain imaging system of claim 2, wherein a bottom surface of the cylindrical casing of the light source probe, and a bottom surface of the cylindrical casing of the photoelectric detector are each provided with eight holes to mount dry electrode electroencephalogram sensors for collecting electroencephalogram signals, wherein each of the dry electrode electroencephalogram sensors adopts a probe structure with an adjustable length.

* * * * *